United States Patent [19]

Leppard et al.

[11] Patent Number: 5,721,292

[45] Date of Patent: Feb. 24, 1998

[54] ACYLPHOSPHINE OXIDES

[75] Inventors: David George Leppard, Marly, Switzerland; Manfred Köhler, Freiburg, Germany; Gebhard Hug, Fribourg, Switzerland

[73] Assignee: Ciba Specialty Chemicals Corporation, Tarrytown, N.Y.

[21] Appl. No.: 793,269

[22] PCT Filed: Aug. 29, 1995

[86] PCT No.: PCT/EP95/03392

§ 371 Date: Mar. 5, 1997

§ 102(e) Date: Mar. 5, 1997

[87] PCT Pub. No.: WO96/07662

PCT Pub. Date: Mar. 14, 1996

[30] Foreign Application Priority Data

Sep. 8, 1994 [CH] Switzerland ............... 2750/94

[51] Int. Cl.⁶ ............... C08G 18/10; C07F 9/53
[52] U.S. Cl. ............... 522/64; 568/14; 568/17; 546/22; 548/530; 549/6; 549/218; 522/63
[58] Field of Search ............... 568/14, 17; 546/22; 548/530; 549/6, 218; 522/63, 64

[56] References Cited

U.S. PATENT DOCUMENTS

| | | | |
|---|---|---|---|
| 4,292,152 | 9/1981 | Lechtken . | |
| 4,324,744 | 4/1982 | Lechtken . | |
| 4,719,297 | 1/1988 | Henne | 544/107 |
| 4,985,472 | 1/1991 | Aosai | 522/64 |
| 5,218,009 | 6/1993 | Rutsch | 522/16 |
| 5,399,770 | 3/1995 | Leppard | 568/15 |
| 5,410,060 | 4/1995 | Schroeder | 546/21 |
| 5,414,133 | 5/1995 | Hall | 568/15 |
| 5,472,992 | 12/1995 | Leppard | 522/18 |
| 5,532,112 | 7/1996 | Kohler | 430/281.1 |

Primary Examiner—C. Warren Ivy
Assistant Examiner—Jean Hollano
Attorney, Agent, or Firm—Victoria M. Malia

[57] ABSTRACT

Compounds of formula (I), in which X is oxygen or sulfur, $R_1$, $R_2$ and $R_3$ independently of one another are a group (a), $C_2$–$C_8$alkenyl, phenyl which is unsubstituted or is substituted from one to four times with $C_1$–$C_{12}$alkyl, $C_1$–$C_{12}$alkoxy, $C_1$–$C_6$alkylthio and/or halogen, or are naphthyl which is unsubstituted or is substituted from one to four times with $C_1$–$C_{12}$alkyl, $C_1$–$C_{12}$alkoxy, $C_1$–$C_6$alkylthio and/or halogen, or are biphenyl which is unsubstituted or is substituted from one to four times with $C_1$–$C_{12}$alkyl, $C_1$–$C_{12}$alkoxy, $C_1$–$C_6$-alkylthio and/or halogen, or $R_1$, $R_2$ and $R_3$ independently of one another are an O-, S- or N-containing 5- or 6-membered heterocyclic ring, $R_1$ is in addition a group of formula (II), or $R_1$ and $R_2$ are linked to form a ring containing 4 to 10 carbon atoms which is unsubstituted or substituted by 1 to 6 $C_1$–$C_4$alkyl groups, $R_4$, $R_5$ and $R_6$ independently of one another are hydrogen or $C_1$–$C_{18}$alkyl, or $R_5$ and $R_6$, together with the carbon atom to which they are attached, form a cyclopropyl, cyclopentyl or cyclohexyl ring, and $R_7$, $R_8$, $R_9$ and $R_{10}$ independently of one another are hydrogen, $C_1$–$C_4$alkyl, $C_1$–$C_4$alkoxy or halogen, are suitable as photoinitiators for the photopolymerization of ethylenically unsaturated systems.

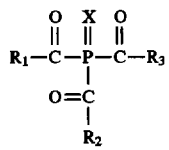

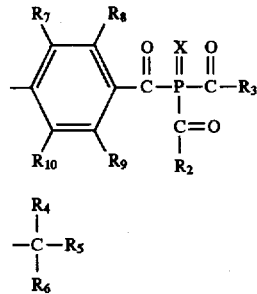

21 Claims, No Drawings

ACYLPHOSPHINE OXIDES

This is the National Stage Application of PCT/EP95/03392 filed Aug. 29, 1995 now WO96/07662 published Mar. 14, 1996.

The invention relates to novel trisacylphosphine oxides, to their use as photoinitiators and to photopolymerizable compositions comprising the compounds according to the invention.

Acylphosphine oxides are known as photoinitiators. U.S. Pat. No. 4,298,738 discloses monoacylphosphine oxides, while U.S. Pat. Nos. 4,737,593 and 4,792,632 disclose bisacylphosphine oxides, in all cases as photoinitiators. In Inorg. Chim. Acta 76(5–6), L273,274 (1983), C. M. Demanet describes trisdimethylamidophosphine oxide as a ligand in uranyl complexes for analysis by photoelectron spectroscopy. At. Energ. 28(5), 383–8 (1970) (=Chem. Abstr. Vol. 73, 92156p (1970)) discloses further tris-substituted phosphine oxides as extractants for uranium. Chem. Abstr. Vol. 95 (97911v (1981) describes the preparation of [($C_2H_5O$)$_3$—PO—]$_2$CO. From U.S. Pat. No. 3,668,093, trisbenzoylphosphine is known as a photoinitiator. In Phosphorus, Sulfur, and Silicon, 1993, Vol. 85, 193–205, J. R. Goerlich et al. describe the synthesis of tris(1-adamantoyl)phosphine oxide.

For the extensive range of application of photoinitiators, there continues to be a need for effective photoinitiators.

It has been found that trisacylphosphine oxide compounds are effective photoinitiators. The invention therefore specifically relates to compounds of the formula I

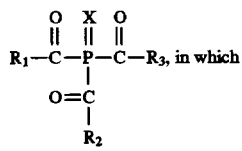

X is oxygen or sulfur, $R_1$, $R_2$ and $R_3$ independently of one another are a group

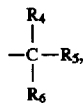

$C_2$–$C_8$alkenyl, phenyl which is unsubstituted or is substituted from one to four times with $C_1$–$C_{12}$alkyl, $C_1$–$C_{12}$alkoxy, $C_1$–$C_6$alkylthio and/or halogen, or are naphthyl which is unsubstituted or is substituted from one to four times with $C_1$–$C_{12}$alkyl, $C_1$–$C_{12}$alkoxy, $C_1$–$C_6$alkylthio and/or halogen, or are biphenyl which is unsubstituted or is substituted from one to four times with $C_1$–$C_{12}$alkyl, $C_1$–$C_{12}$alkoxy, $C_1$–$C_6$alkylthio and/or halogen, or $R_1$, $R_2$ and $R_3$ independently of one another are an O-, S- or N-containing 5- or 6-membered heterocyclic ring, $R_1$ is in addition a group of the formula II

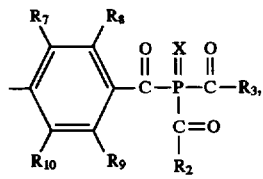

or $R_1$ and $R_2$ are linked to form a ring containing 4 to 10 carbon atoms which is unsubstituted or substituted by 1 to 6 $C_1$–$C_4$alkyl groups, $R_4$, $R_5$ and $R_6$ independently of one another are hydrogen or $C_1$–$C_{18}$alkyl, or $R_5$ and $R_6$, together with the carbon atom to which they are attached, form a cyclopropyl, cyclopentyl or cyclohexyl ring, and $R_7$, $R_8$, $R_9$ and $R_{10}$ independently of one another are hydrogen, $C_1$–$C_4$alkyl, $C_1$–$C_4$alkoxy or halogen.

$C_1$–$C_{12}$alkyl may be linear or branched and is for example methyl, ethyl, n-propyl, isopropyl, n-butyl, isobutyl, sec-butyl, tert-butyl, pentyl, hexyl, heptyl, octyl, 2,4,4-trimethylpent-1-yl, 2-ethylhexyl, nonyl, decyl or dodecyl. In addition, $C_1$–$C_{18}$alkyl is for example tetradecyl, heptadecyl or octadecyl.

$C_1$–$C_{12}$Alkoxy is for example methoxy, ethoxy, n-propoxy, isopropoxy, butyloxy, octyloxy, decyloxy or dodecyloxy, especially $C_1$–$C_4$alkoxy and preferably methoxy.

$C_1$–$C_6$Alkylthio is for example methylthio, ethylthio, n-propylthio, isopropylthio, butylthio or hexylthio.

$C_2$–$C_8$Alkenyl is for example vinyl, allyl, methallyl, 1,1-dimethallyl, 2-butenyl, 2-hexenyl or octenyl.

Halogen is fluorine, chlorine, bromine or iodine, especially chlorine.

Phenyl substituted from one to four times with halogen, $C_1$–$C_{12}$alkyl and/or $C_1$–$C_{12}$alkoxy is for example chlorophenyl, dichlorophenyl, tetrachlorophenyl, tolyl, dimethylphenyl, mesityl, tetramethylphenyl, ethylphenyl, diethylphenyl, triethylphenyl, methylethylphenyl, dimethylethylphenyl, methoxyphenyl, dimethoxyphenyl, trimethoxyphenyl, dimethoxymethylphenyl, methoxymethylphenyl, dimethylmethoxyphenyl, ethoxyphenyl, diethoxyphenyl, diethoxymethylphenyl, propyloxyphenyl, butoxyphenyl, dibutoxyphenyl, butoxymethoxyphenyl, ethoxymethoxyphenyl, butoxyethoxyphenyl, preferably tolyl.

Phenyl, naphthyl or biphenyl radicals are unsubstituted or are substituted from one to four times, preferably from one to three times, and in particular two or three times.

$R_1$, $R_2$ and $R_3$ as an O-, S- or N-containing 5- or 6-membered heterocyclic ring are for example a pyridyl, furyl, pyrrolyl or thienyl ring.

Where $R_1$ and $R_2$ are linked to form a ring containing 4 to 10 carbon atoms this ring may include the phosphorus and the two carbonyl carbon atoms to which $R_1$ and $R_2$ are attached, but may also be adjacent to the two carbonyl carbon atoms. In such cases, the ring may be aliphatic or aromatic and is for example cyclohexyl or benzyl. In this case, the following compounds, for example, are involved.

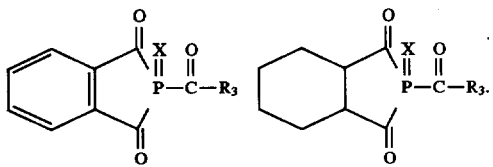

Preference is given to compounds of the formula I in which $R_1$, $R_2$ and $R_3$ are phenyl which is substituted at least in position 2.

Preference is given to compounds of the formula I in which $R_1$, $R_2$ and $R_3$ independently of one another are a group

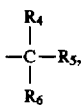

$C_2$–$C_6$alkenyl, naphthyl which is unsubstituted or is substituted from one to four times with $C_1$–$C_4$alkyl, $C_1$–$C_4$alkoxy or halogen, biphenyl which is unsubstituted or is substituted from one to four times with $C_1$–$C_4$alkyl, $C_1$–$C_4$alkoxy or halogen, or are a radical of the formula III

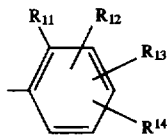

or are pyridyl, furyl, pyrrolyl or thienyl, $R_1$ in addition is a group of the formula II, or $R_1$ and $R_2$ are linked to form a benzene ring, $R_4$ and $R_5$ independently of one another are hydrogen or $C_1$–$C_{12}$alkyl, $R_6$ is $C_1$–$C_{12}$alkyl, or $R_5$ and $R_6$, together with the carbon atom to which they are attached, form a cyclopentyl or cyclohexyl ring, $R_7$, $R_8$, $R_9$ and $R_{10}$ independently of one another are methyl or methoxy, $R_{11}$ is $C_1$–$C_4$alkyl, $C_1$–$C_4$alkoxy, $C_1$–$C_4$alkylthio or halogen, and $R_{12}$, $R_{13}$ and $R_{14}$ independently of one another are hydrogen, $C_1$–$C_4$alkyl, $C_1$–$C_4$alkoxy, $C_1$–$C_4$alkylthio or halogen.

Further compounds of the formula I which are of interest are those in which $R_1$, $R_2$ and $R_3$ independently of one another are a group

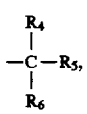

$C_2$–$C_4$alkenyl or a radical of the formula III, $R_4$ is hydrogen, $R_5$ and $R_6$ are $C_1$–$C_7$alkyl, or $R_5$ and $R_6$, together with the carbon atom to which they are attached, form a cyclopentyl or cyclohexyl ring, $R_{11}$ is $C_1$–$C_4$alkyl, $C_1$–$C_4$alkoxy or chlorine, and $R_{12}$, $R_{13}$ and $R_{14}$ independently of one another are hydrogen, $C_1$–$C_4$alkyl, $C_1$–$C_4$alkoxy or chlorine.

Compounds of the formula I meriting particular attention are those in which $R_1$, $R_2$ and $R_3$ are identical and are tert-butyl, $C_2$–$C_4$alkenyl or a radical of the formula III, $R_{11}$ is methyl, methoxy or chlorine, and $R_{12}$, $R_{13}$ and $R_{14}$ independently of one another are hydrogen, methyl, methoxy or chlorine.

Particular preference is given to those compounds of the formula I in which $R_1$, $R_2$ and $R_3$ are identical and are a radical of the formula IV

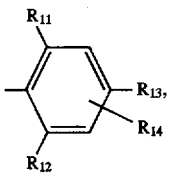

$R_{11}$ is methyl, methoxy or chlorine, $R_{12}$ is hydrogen, $R_{13}$ is hydrogen or methyl, and $R_{14}$ is hydrogen.

Preferred compounds of the formula I are those in which X is oxygen.

Further preferred are compounds wherein $R_1$, $R_2$ and $R_3$ have the same meaning.

Examples of compounds according to the invention are tris(benzoyl)phosphine oxide tris(2-methylbenzoyl)phosphine oxide tris(2,6-dimethylbenzoyl)phosphine oxide tris(2,4,6-trimethylbenzoyl)phosphine oxide tris(2-methoxybenzoyl)phosphine oxide tris(2,4-dimethoxybenzoyl)phosphine oxide tris(2,6-dimethoxybenzoyl)phosphine oxide tris(2-chlorobenzoyl)phosphine oxide tris(2,4-dichlorobenzoyl)phosphine oxide tris(2,6-dichlorobenzoyl)phosphine oxide tris(2,3,4,6-tetramethylbenzoyl)phosphine oxide tris(tert.-butylcarbonyl)phosphine oxide tris(allylcarbonyl)phosphine oxide tris(methallylcarbonyl)phosphine oxide bis(2,4,6-trimethylbenzoyl)-2,6-dimethoxybenzoylphosphine oxide tris(benzoyl)phosphine sulfide tris(2-methylbenzoyl)phosphine sulfide tris(2,6-dimethylbenzoyl)phosphine sulfide tris(2,4,6-trimethylbenzoyl)phosphine sulfide tris(2-methoxybenzoyl)phosphine sulfide tris(2,4-dimethoxybenzoyl)phosphine sulfide tris(2,6-dimethoxybenzoyl)phosphine sulfide tris(2-chlorobenzoyl)phosphine sulfide tris(2,4-dichlorobenzoyl)phosphine sulfide tris(2,6-dichlorobenzoyl)phosphine sulfide tris(2,3,4,6-tetramethylbenzoyl)phosphine sulfide tris(tert-butylcarbonyl)phosphine sulfide tris(allylcarbonyl)phosphine sulfide tris(methallylcarbonyl)phosphine sulfide bis(2,4,6-trimethylbenzoyl)-2,6-dimethoxybenzoylphosphine sulfide The compounds of the formula I can be obtained by first of all preparing the appropriately substituted phosphine and then reacting this to give the oxide or sulfide.

A) Preparation of the phosphines

The phosphines can be obtained, for example, by reacting an acyl chloride with lithium phosphide, sodium phosphide or sodium/potassium phosphide (1)

$R$ is $R_1$, $R_2$ and $R_3$ as defined above

A is Li, Na or Na/K

Another possible method of preparation is, for example, to react an acyl chloride with tristrimethylsilylphosphine (2):

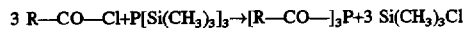

The trisacylphosphines can also be obtained, for example, by reacting an acyl chloride with phosphine (3):

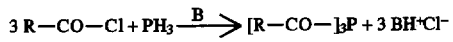

B is a base.

Examples of suitable bases are tertiary amines, pyridine, alkali metals, lithium diisopropylamide, alkali metal alcoholates or alkali metal hydrides. The reaction is preferably carried out in solution. Particularly suitable solvents are hydrocarbons such as, for example, alkanes, benzene, toluene or xylene. After the base chloride formed has been separated off, the trisacylphosphine can be isolated by evaporation, or the reaction to give the oxide or sulfide is carried out with the solution of the crude product, without isolating the trisacylphosphine.

The reaction temperatures are advantageously in the range from room temperature to 100° C.

For the preparation of "mixed" phosphines, it is advantageous to use mixtures of the corresponding acyl chlorides.

However, it is also possible to carry out the acylation reaction by a stepwise procedure in accordance with the equations below. In this case, lithium bistrimethylsilylphosphide is reacted with the respective acyl chlorides:

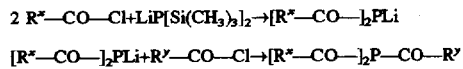

$R^x$ and $R^y$ are in each case different radicals $R_1$, $R_2$ und $R_3$.

B1) Reaction to the oxide

The reaction of the trisacylphosphines to give the oxide is advantageously carried out, for example, by reaction with hydrogen peroxide.

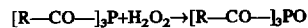

or

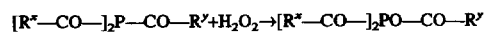

Suitable oxidizing agents for this reaction stage are hydrogen peroxide and organic peroxy compounds, for example peracetic acid. However, it is also possible to carry out the oxidation step by passing in oxygen. This is advantageously carried out in the solvent from the preceding reaction stage.

B2) Reaction to the sulfide

The trisacylphosphine sulfides are obtained, for example, by reacting the phosphine compounds with elemental sulfur:

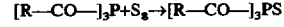

or

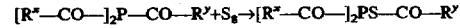

This preparation method is described, for example, for monoacylphosphine sulfides in DE-A-3 034 697. The trisacylphosphines are reacted, in bulk or if desired in a suitable inert organic solvent, for example a hydrocarbon such as toluene, cyclohexane or chlorobenzene, or an aliphatic or aromatic ether such as dibutyl ether, dioxane, diethylene glycol dimethyl ether or diphenyl ether, with an equimolar quantity of elemental sulfur. The trisacylphosphine sulfide formed or its solution is separated from any sulfur still present by filtration. The reaction is advantageously carried out in an inert gas atmosphere of, for example, nitrogen, argon or carbon dioxide, preferably nitrogen. Depending on the solvent and the starting materials used, the reaction temperatures are between 20° and 200° C., especially from 60° to 120° C. Following the removal of the solvent, the trisacylphosphine sulfide formed can be isolated in pure form by distillation or recrystallization.

The preparation of the acyl chlorides is familiar to the person skilled in the art and is carried out by known methods of the prior art.

The synthesis of lithium phosphide is described, for example, in Ber. 92 (1952), 1118. The preparation of sodium/potassium phosphide is described, for example, in Inorg. Synth. 27, 243. The same reference contains a synthesis for tristrimethylsilylphosphine. A further preparation method for this compound is indicated, for example, in Chem. Ber. 108 (1975), 2484.

Lithium bistrimethylsilylphosphine is prepared, for example, by the method described in Z. Anorg. Allgem. Chem. 42 (1976), 104.

In accordance with the invention, the compounds of the formula I can be used as photoinitiators for the photopolymerization of ethylenically unsaturated compounds or of mixtures which contain such compounds.

This use may also be practised in combination with another photoinitiator and/or with other additives.

The invention therefore also relates to photopolymerizable compositions comprising (a) at least one ethylenically unsaturated photopolymerizable compound, and (b) as photoinitiator, at least one compound of the formula I it being possible for the composition to contain other photoinitiators and/or other additives in addition to component (b).

The unsaturated compounds may contain one or more olefinic double bonds. They may be of low molecular weight (monomeric) or of relatively high molecular weight (oligomeric). Examples of monomers containing a double bond are alkyl or hydroxyalkyl acrylates or methacrylates, for example methyl, ethyl, butyl, 2-ethylhexyl or 2-hydroxyethyl acrylate, isobornyl acrylate, methyl methacrylate or ethyl methacrylate. Silicone acrylates are also of interest. Further examples are acrylonitrile, acrylamide, methacrylamide, N-substituted (meth)acrylamides, vinyl esters such as vinyl acetate, vinyl ethers such as isobutyl vinyl ether, styrene, alkylstyrenes and halostyrenes, N-vinylpyrrolidone, vinyl chloride or vinylidene chloride.

Examples of monomers containing two or more double bonds are the diacrylates of ethylene glycol, propylene glycol, neopentylglycol, hexamethylene glycol or bisphenol A, and also 4,4'-bis(2-acryloyloxyethoxy)diphenylpropane, trimethylolpropane triacrylate, pentaerythritol triacrylate or pentaerythritol tetraacrylate, vinyl acrylate, divinylbenzene, divinyl succinate, diallyl phthalate, triallyl phosphate, triallyl isocyanurate or tris(2-acryloylethyl) isocyanurate.

Examples of relatively high molecular weight (oligomeric) polyunsaturated compounds are acrylicized epoxy resins, and polyesters, polyurethanes and polyethers which are acrylicized or contain vinyl ether or epoxy groups. Further examples of unsaturated oligomers are unsaturated polyester resins which are mostly prepared from maleic acid, phthalic acid and one or more diols and have molecular weights of from about 500 to 3000. In addition it is also possible to employ vinyl ether monomers and vinyl ether oligomers, and also maleate-terminated oligomers having polyester, polyurethane, polyether, polyvinyl ether and epoxy main chains. Combinations of vinyl ether group-containing oligomers and polymers as are described in WO 90/01512 are particularly highly suitable. However, copolymers of vinyl ether and maleic acid-functionalized monomers are also appropriate. Such unsaturated oligomers can also be referred to as prepolymers.

Examples of particularly suitable compounds are esters of ethylenically unsaturated carboxylic acids and polyols or polyepoxides, and polymers containing ethylenically unsaturated groups in the chain or in the side groups, for example unsaturated polyesters, polyamides and polyurethanes and copolymers thereof, polybutadiene and butadiene copolymers, polyisoprene and isoprene copolymers, polymers and copolymers containing (meth)acrylic groups in the side chains, and mixtures of one or more such polymers.

Examples of unsaturated carboxylic acids are acrylic acid, methacrylic acid, crotonic acid, itaconic acid, cinnamic acid, and unsaturated fatty acids such as linolenic acid or oleic acid. Acrylic acid and methacrylic acid are preferred.

Suitable polyols are aromatic and, in particular, aliphatic and cycloaliphatic polyols. Examples of aromatic polyols are hydroquinone, 4,4'-dihydroxybiphenyl, 2,2-di(4-hydroxyphenyl)propane, and also novolaks and resols. Examples of polyepoxides are those based on said polyols, especially aromatic polyols and epichlorohydrin. Other suitable polyols include polymers and copolymers which contain hydroxyl groups in the polymer chain or in side groups, for example polyvinyl alcohol and copolymers thereof or hydroxyalkyl polymethacrylates or copolymers thereof. Other suitable polyols are oligoesters containing hydroxyl end groups.

Examples of aliphatic and cycloaliphatic polyols are alkylenediols, preferably having 2 to 12 carbon atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycol having molecular weights of preferably from 200 to 1500, 1,3-cyclopentanediol, 1,2-, 1,3- or 1,4-cyclohexanediol, 1,4-dihydroxymethylcyclohexane, glycerol, tris(β-hydroxyethyl)amine, trimethylolethane, trimethylolpropane, pentaerythritol, dipentaerythritol and sorbitol.

The polyols may be partially or fully esterified by means of one or more unsaturated carboxylic acids, where the free hydroxyl groups in partial esters may be modified, for example etherified or esterified with other carboxylic acids.

Examples of esters are:
trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetramethacrylate, sorbitol pentaacrylate, sorbitolhexaacrylate, oligoester acrylates and methacrylates, glycerol di- and triacrylate, 1,4-cyclohexane diacrylate, bisacrylates and bismethacrylates of polyethylene glycol having molecular weights of from 200 to 1500, or mixtures thereof.

Further suitable components (a) are the amides of identical or different unsaturated carboxylic acids of aromatic, cycloaliphatic and aliphatic polyamines, preferably having 2 to 6, in particular 2 to 4, amino groups. Examples of polyamines of this type are ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, di-β-aminoethyl ether, diethylenetriamine, triethylenetetramine, di(β-aminoethoxy) or di(β-aminopropoxy)ethane. Other suitable polyamines are polymers and copolymers which may contain additional amino groups in the side chain, and oligoamides containing amino end groups. Examples of unsaturated amides of this type are: methylenebisacrylamide, 1,6-hexamethylenebisacrylamide, diethylenetriaminetrismethacrylamide, bis (methacrylamidopropoxy)ethane, β-methacrylamidoethyl methacrylate, and N-[(β-hydroxyethoxy)ethyl]acrylamide.

Suitable unsaturated polyesters and polyamides are derived, for example, from maleic acid and diols or diamines. Some of the maleic acid may be replaced by other dicarboxylic acids. They can be employed together with ethylenically unsaturated comonomers, for example styrene. The polyesters and polyamides may also be derived from dicarboxylic acids and ethylenically unsaturated diols or diamines, in particular from relatively long chain compounds containing, for example, 6 to 20 carbon atoms. Examples of polyurethanes are those built up from saturated or unsaturated diisocyanates and from unsaturated or saturated diols.

Polybutadiene and polyisoprene and copolymers thereof are known. Examples of suitable comonomers are olefins such as ethylene, propene, butene, hexene, (meth)acrylate, acrylonitrile, styrene and vinyl chloride. Polymers containing (meth)acrylate groups in the side chain are also known. These may be, for example, products of the reaction of novolak-based epoxy resins with (meth)acrylic acid, homopolymers or copolymers of vinyl alcohol or hydroxyalkyl derivatives thereof which have been esterified using (meth)acrylic acid, or homopolymers and copolymers of (meth)acrylates which have been esterified using hydroxyalkyl (meth)acrylates.

The photopolymerizable compounds may be employed alone or in any desired mixtures. Preference is given to mixtures of polyol (meth)acrylates.

It is also possible to add binders to the compositions according to the invention; this is particularly expedient if the photopolymerizable compounds are liquid or viscous substances. The quantity of binder may be for example, 5–95% by weight, preferably 10–90% by weight and, in particular, 40–90% by weight, based on the overall solids content. The binder is chosen depending on the field of application and on the properties required therefor, such as the facility for development in aqueous and organic solvent systems, adhesion to substrates and sensitivity to oxygen.

Examples of suitable binders are polymers having a molecular weight of about 5000–2,000,000, preferably 10,000–1,000,000. Examples are homo- and copolymeric acrylates and methacrylates, for example copolymers of methyl methacrylate/ethyl acrylate/methacrylic acid, poly (alkyl methacrylates), poly(alkyl acrylates); cellulose esters and cellulose ethers, such as cellulose acetate, cellulose acetate butyrate, methylcellulose and ethylcellulose; polyvinylbutyral, polyvinylformal, cyclized rubber, polyethers, such as polyethylene oxide, polypropylene oxide and polytetrahydrofuran; polystyrene, polycarbonate, polyurethane, chlorinated polyolefins, polyvinyl chloride, copolymers of vinyl chloride/vinylidene chloride, copolymers of vinylidene chloride with acrylonitrile, methyl methacrylate and vinyl acetate, polyvinyl acetate, copoly (ethylene/vinyl acetate), polymers such as polycaprolactam and poly(hexamethyleneadipamide), and polyesters such as poly(ethylene glycol terephthalate) and poly(hexamethylene glycol succinate).

The unsaturated compounds may also be used in mixtures with non-photopolymerizable film-forming components. These may be, for example, physically drying polymers or solutions thereof in organic solvents, for example nitrocellulose or cellulose acetobutyrate. However, they may also be chemically curable or heat-curable resins such as, for example, polyisocyanates, polyepoxides or melamine resins. The additional use of heat-curable resins is important for use in so-called hybrid systems, which are photopolymerized in a first step and crosslinked by thermal aftertreatment in a second step.

The photopolymerizable mixtures may contain various additives in addition to the photoinitiator. Examples thereof are thermal inhibitors, which are intended to prevent premature polymerization, for example hydroquinone, hydroquinone derivatives, p-methoxyphenol, β-naphthol or sterically hindered phenols such as 2,6-di(tert-butyl)-p-cresol. The shelf life in the dark can be increased, for example, by using copper compounds such as copper naphthenate, copper stearate or copper octanoate, phosphorus compounds, for example triphenylphosphine, tributylphosphine, triethyl phosphite, triphenyl phosphite or tribenzyl phosphite, quaternary ammonium compounds, for example tetramethylammonium chloride or trimethylbenzylammonium chloride, or hydroxylamine derivatives, for example N-diethylhydroxylamine. In order to exclude atmospheric oxygen during the polymerization, paraffin or similar wax-like substances can be added; these migrate to the surface on commencement of the polymerization because of their low solubility in the polymer, and form a transparent surface layer which prevents the ingress of air. Similarly, an oxygen-impermeable layer may be applied. Light stabilizers which can be added in small quantities are UV absorbers, for example those of the hydroxyphenylbenzotriazole, hydroxyphenylbenzophenone, oxalamide or hydroxyphenyl-s-triazine type. These compounds can be employed individually or as mixtures, with or without the use of sterically hindered amines (HALS).

Examples of such UV absorbers and light stabilizers are:
1. 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl) benzotriazole, 2-(2'-hydroxy-4'-octoxyphenyl) benzotriazole, 2-(3',5'-di-tert-amyl-2'-hydroxyphenyl) benzotriazole, 2-(3',5'-bis(α,α-dimethylbenzyl)-2'-hydroxyphenyl)benzotriazole, mixture of 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl) phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, and 2-(3-tert-butyl-2'-hydroxy-5'-(2-isooctyloxycarbonylethyl) phenylbenzotriazole, 2,2'-methylenebis[4-(1,1,3,3-tetramethylbutyl)-6-benzotriazol-2-yl phenol]; transesterification product of 2-[3'-tert-butyl-5'-(2-methoxycarbonylethyl)-2'-hydroxyphenyl]benzotriazole with polyethylene glycol 300; [R—CH$_2$CH$_2$—COO(CH$_2$)$_3$]$_2$ where R=3'-tert-butyl-4'-hydroxy-5'-2H benzotriazol-2-yl phenyl.

2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivatives.

3. Esters of unsubstituted or substituted benzoic acids, for example 4-tert-butyl-phenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

4. Acrylates, for example ethyl and isooctyl α-cyano-β,β-diphenylacrylate, methyl α-carbomethoxycinnamate, methyl and butyl α-cyano-β-methyl-p-methoxycinnamate, methyl α-carbomethoxy-p-methoxycinnamate and N-(β-carbomethoxy-β-cyanovinyl)-2-methylindoline.

5. Sterically hindered amines, for example bis(2,2,6,6-tetramethylpiperidyl) sebacate, bis(2,2,6,6-tetramethylpiperidyl) succinate, bis(1,2,2,6,6-pentamethylpiperidyl) sebacate, bis(1,2,2,6,6-pentamethylpiperidyl) n-butyl-3,5-di-tert-butyl-4-hydroxybenzylmalonate, the product of the condensation of 1-hydroxyethyl-2,2,6,6-tetramethyl-4-hydroxypiperidine and succinic acid, the product of the condensation of N,N'-bis(2,2,6,6-tetramethyl-4-piperidyl) hexamethylenediamine and 4-tert-octylamino-2,6-dichloro-1,3,5-s-triazine, tris(2,2,6,6-tetramethyl-4-piperidyl) nitrilotriacetate, tetrakis(2,2,6,6-tetramethyl-4-piperidyl) 1,2,3,4-butanetetraoate, 1,1'-(1,2-ethanediyl)bis-(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl) 2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis (1-octyloxy-2,2,6,6-tetramethylpiperidyl) sebacate, bis (1-octyloxy-2,2,6,6-tetramethylpiperidyl) succinate, the product of the condensation of N,N'-bis(2,2,6,6-tetramethyl-4-piperidyl)hexamethylene diamine and 4-morpholino-2,6-dichloro-1,3,5-triazine, the product of the condensation of 2-chloro-4,6-di(4-n-butylamino-2,2,6,6-tetramethylpiperidyl) 1,3,5-triazine and 1,2-bis (3-aminopropylamino)ethane, the product of the condensation of 2-chloro-4,6-di(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl) pyrrolidine-2,5-dione, 3-dodecyl-1-(1,2,2,6,6-pentamethyl-4-piperidyl)pyrrolidine-2,5-dione.

6. Oxalamides, for example 4,4'-dioctyloxyoxanilide, 2,2'-diethoxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylaminopropyl)oxalamide, 2-ethoxy-5-tert-butyl-2'-ethyloxanilide and mixtures thereof with 2-ethoxy-2'-ethyl-5,4'-di-tert-butyloxanilide, and mixtures of o- and p-methoxy- and of o- and p-ethoxy-disubstituted oxanilides.

7. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxyl4-(2-hydroxyl3-butyloxypropyloxy) phenyl]-4,6-bis(2,4-dimethylphenyl)-1,3,5-triazine, 2-[2-hydroxyl4-(2-hydroxy-3-octyloxy-propyloxy) phenyl]-4,6-bis(2,4-dimethylphenyl)-1,3,5-triazine and 2-[4-dodecyl/tridecyloxy(2-hydroxypropyl)oxy-2-hydroxyphenyl]-4,6-bis(2,4-dimethylphenyl)-1,3,5-triazine.

8. Phosphites and phosphonites, for example triphenyl phosphite, diphenyl alkyl phosphite, phenyl dialkylphosphite, tris-(nonylphenyl) phosphite, trilauryl phosphite, trioctadecyl phosphite, distearyl pentaerythrityl diphosphite, tris(2,4-di-tert-butylphenyl) phosphite, diisodecylpentaerythrityl diphosphite, bis(2,4-di-tert-butylphenyl) pentaerythrityl diphosphite, bis(2,6-di-tert-butyl-4-methylphenyl) pentaerythrityl diphosphite, bisisodecyloxypentaerythrityl diphosphite, bis(2,4-di-tert-butyl-6-methylphenyl) pentaerythrityl diphosphite, bis(2,4,6-tri-tert-butylphenyl) pentaerythrityl diphosphite, tristearyl sorbitol triphosphite, tetrakis-(2,4-di-tert-butylphenyl)-4,4'-biphenylenediphosphonite, 6-isooctyloxy-2,4,8,10-tetra-tert-butyl-12H-dibenz[d,g]-1,3,2-dioxaphosphocine, 6-fluoro-2,4,8,10-tetra-tert-butyl-12-methyl-dibenz[d,g]-1,3,2-dioxaphosphocine, bis(2,4-di-tert-butyl-6-methylphenyl)methyl phosphite, and bis(2,4-di-tert-butyl-6-methylphenyl) ethyl phosphite.

To accelerate the photopolymerization it is possible to add amines, for example triethanolamine, N-methyldiethanolamine, ethyl p-dimethylaminobenzoate or Michler's ketone. The action of the amines can be intensified by the addition of aromatic ketones of the benzophenone type. Examples of amines which can be used as oxygen scavengers are substituted N,N-dialkylanilines as described in EP-A-339 841. Further accelerators, coinitiators and autoxidizers are thiols, thioethers, disulfides and phosphines as described, for example, in EP-A-438 123 and GB-A-21 80 358.

The photopolymerization can also be accelerated by the addition of photosensitizers which shift or broaden the spectral sensitivity. These are, in particular, aromatic carbonyl compounds such as benzophenone derivatives, thioxanthone derivatives, anthraquinone derivatives and 3-acylcoumarin derivatives and 3-(aroylmethylene) thiazolines, and also eosine, rhodanine and erythrosine dyes.

The curing process may be assisted, in particular, by compositions which are pigmented (for example with $TiO_2$), but also by the addition of a component which forms free radicals under thermal conditions, for example an azo compound such as 2,2'-azobis(4-methoxy-2,4-dimethylvaleronitrile), a triazene, diazo sulfide, pentazadiene or a peroxy compound such as a hydroperoxide or peroxycarbonate, for example t-butyl hydroperoxide, as described in EP-A 245 639, for example.

The compositions according to the invention may also contain a photoreducible dye, for example xanthene, benzoxanthene, benzothioxanthene, thiazine, pyronine, porphyrin or acridine dyes, and/or a trihalomethyl compound which can be cleaved by radiation. Similar compositions are described in, for example, EP-A-445 624.

Other conventional additives are—depending on the application—optical brighteners, fillers, pigments, dyes, wetting agents or levelling assistants.

Thick and pigmented coatings can suitably be cured by the addition of glass microbeads or powdered glass fibres, as described in U.S. Pat. No. 5,013,768, for example.

The invention also relates to compositions comprising as component (a) at least one ethylenically unsaturated, photopolymerizable compound which is emulsified or dissolved in water.

Radiation-curable, aqueous prepolymer dispersions of this type are commercially available in many variations. This term is taken to mean a dispersion of water and at least one prepolymer dispersed therein. The concentration of the water in these systems is, for example, from 5 to 80% by weight, in particular from 30 to 60% by weight. The radiation-curable prepolymer or prepolymer mixture is present, for example, in concentrations of from 95 to 20% by weight, in particular from 70 to 40% by weight. The total of the percentages indicated for water and prepolymer in these compositions is in each case 100, to which are added the auxiliaries and additives in various amounts depending on the application.

The radiation-curable, water-dispersed, film-forming prepolymers, which are frequently also dissolved, are, for aqueous prepolymer dispersions, monofunctional or polyfunctional ethylenically unsaturated prepolymers which are known per se, can be initiated by means of free radicals and contain, for example, from 0.01 to 1.0 mol of polymerizable double bonds per 100 g of prepolymer, and have an average molecular weight of, for example, at least 400, in particular from 500 to 10,000. Depending on the intended application, however, prepolymers having higher molecular weights may also be suitable. For example, polyesters containing polymerizable C—C double bonds and having a maximum acid number of 10, polyethers containing polymerizable C—C double bonds, hydroxyl-containing products of the reaction of a polyepoxide containing at least two epoxide groups per molecule with at least one α,β-ethylenically unsaturated carboxylic acid, polyurethane (meth)acrylates and α,β-ethylenically unsaturated acrylic copolymers containing acrylic radicals, as described in EP-A-12 339, are used. Mixtures of these prepolymers may also be used. Also suitable are the polymerizable prepolymers described in EP-A-33 896, which are thioether adducts of polymerizable prepolymers having an average molecular weight of at least 600, a carboxyl group content of from 0.2 to 15% and a content of from 0.01 to 0.8 mol of polymerizable C—C double bonds per 100 g of prepolymer. Other suitable aqueous dispersions based on specific alkyl (meth)acrylate polymers are described in EP-A-41 125, and suitable water-dispersible, radiation-curable prepolymers made from urethane acrylates are disclosed in DE-A-2 936 039. These radiation-curable, aqueous prepolymer dispersions may contain, as further additives, dispersion assistants, emulsifiers, antioxidants, light stabilizers, dyes, pigments, fillers, for example talc, gypsum, silica, rutile, carbon black, zinc oxide and iron oxides, reaction accelerators, levelling agents, lubricants, wetting agents, thickeners, matting agents, antifoams and other assistants which are conventional in surface-coating technology. Suitable dispersion assistants are water-soluble, high molecular weight organic compounds containing polar groups, for example polyvinyl alcohols, polyvinylpyrrolidone and cellulose ethers. Emulsifiers which can be used are nonionic emulsifiers and possibly also ionic emulsifiers.

The photopolymerizable compositions contain the photoinitiator (b) advantageously in a quantity of from 0.05 to 15% by weight, preferably from 0.1 to 5% by weight, based on the composition.

Compounds of the formula I in which $R_1$, $R_2$ and/or $R_3$ are $C_2$–$C_8$alkenyl can be polymerized alone or together with other ethylenically unsaturated compounds.

In certain cases it may be of advantage to use mixtures of two or more of the photoinitiators according to the invention. It is of course also possible to use mixtures with known photoinitiators, for example mixtures with benzophenone, acetophenone derivatives, for example α-hydroxycycloalkylphenyl ketones, dialkoxyacetophenones, α-hydroxy- or α-aminoacetophenones, 4-aroyl-1,3-dioxolanes, benzoin alkyl ethers and benzil ketals, monoacylphosphine oxides, bisacylphosphine oxides or titanocenes. When the photoinitiators according to the invention are employed in hybrid systems, cationic photoinitiators such as benzoyl peroxide, aromatic sulfonium or iodonium salts or cyclopentadienylareneiron(II) complex salts are used in addition to the free-radical curing agents according to the invention.

The invention also specifically relates to compositions in which the additional photoinitiators are compounds of the formula V

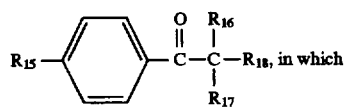

$R_{15}$ is hydrogen, $C_1$–$C_{18}$alkyl, $C_1$–$C_{18}$alkoxy, —OCH$_2$CH$_2$—OR$_{19}$, a group

or a group

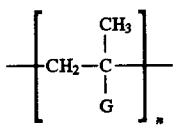

in which has a value from 2 to 10 and and G is the radical

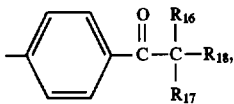

$R_{16}$ and $R_{17}$ independently of one another are hydrogen, $C_1$–$C_6$alkyl, phenyl, $C_1$–$C_{16}$alkoxy or —O(CH$_2$CH$_2$O)$_m$—$C_1$–$C_{16}$alkyl in which m is a number from 1–20, or $R_{16}$ and $R_{17}$, together with the carbon atom to which they are attached, form a cyclohexyl ring, $R_{18}$ is hydroxyl, $C_1$–$C_{16}$alkoxy or —O(CH$_2$CH$_2$O)$_m$$C_1$–$C_{16}$alkyl, $R_{16}$, $R_{17}$ and $R_{18}$ not all simultaneously being $C_1$–$C_{16}$alkoxy or —O(CH$_2$CH$_2$O)$_m$—$C_1$–$C_{16}$alkyl, and $R_{19}$ is hydrogen,

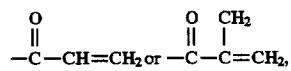

or in which the additional photoinitiators are compounds of the formula VI

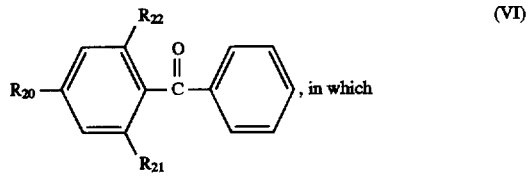

$R_{20}$, $R_{21}$ and $R_{22}$ independently of one another are hydrogen or methyl,
or in which the additional photoinitiators are mixtures of compounds of the formulae V and/or VI.

$C_1$–$C_{18}$Alkyl $R_{15}$ may be as defined for $R_1$. $C_1$–$C_6$Alkyl $R_{16}$ and $R_{17}$ and $C_1$–$C_4$alkyl $R_{18}$, likewise, may be as defined for $R_1$, except for the respective number of carbon atoms.

$C_1$–$C_{18}$Alkoxy $R_{15}$ is, for example, branched or unbranched alkoxy such as methoxy, ethoxy, n-propoxy, isopropoxy, n-butoxy, isobutoxy, sec-butoxy, tert-butoxy, pentyloxy, hexyloxy, heptyloxy, octyloxy, 2,4,4-trimethylpent-1-yloxy, 2-ethylhexyloxy, nonyloxy, decyloxy, dodecyloxy or octadecyloxy.

$C_1$–$C_{16}$Alkoxy $R_{16}$, $R_{17}$ and $R_{18}$ may be as defined for $R_{15}$ except for the appropriate number of carbon atoms; they are preferably decyloxy, methoxy and ethoxy, especially methoxy and ethoxy.

The radical O(CH$_2$CH$_2$O)$_m$—$C_1$–$C_{16}$alkyl represents 1 to 20 successive ethylene oxide units whose chain is terminated by a $C_1$–$C_{16}$alkyl radical. m is preferably from 1 to 10, for example 1 to 8, especially 1 to 6. The chain of ethylene oxide units is preferably terminated by a $C_1$–$C_{10}$alkyl radical, for example a $C_1$–$C_8$alkyl radical, in particular a $C_1$–$C_4$alkyl radical.

Preference is given to compositions in which $R_{16}$ and $R_{17}$ in the formula V are independently of one another $C_1$–$C_6$alkyl or, together with the carbon atom to which they are attached, form a cyclohexyl ring, and $R_{18}$ is hydroxyl.

Further preferred compositions are those in which the proportion of compounds of the formula I in the mixture with compounds of the formulae V and/or VI is from 5 to 95%, preferably from 30 to 70%.

Other important compositions are those in which $R_{16}$ and $R_{17}$ in the compounds of the formula V are identical and are methyl, and $R_{18}$ is hydroxyl or isopropoxy.

Preference is likewise given to compositions comprising compounds of the formula I and a mixture of compounds of the formula VI in which compounds of the formula VI where $R_{20}$ and $R_{21}$ are hydrogen and $R_{22}$ is methyl are present to the extent of 20% and compounds of the formula VI where $R_{20}$, $R_{21}$ and $R_{22}$ are methyl are present to the extent of 80%.

Compositions of prime interest are those as described above which contain photoinitiator mixtures of the formulae I, V and/or VI and which are liquid at room temperature.

The preparation of the compounds of the formulae V and VI is known in general terms, and some of the compounds are commercially available. The preparation of oligomeric compounds of the formula V is described, for example, in EP-A-0 161 463. A description of the preparation of the compounds of the formula VI is given, for example, in EP-A-209 831.

The photopolymerizable compositions can be used for various purposes, for example as printing inks, as varnishes or clearcoats, as white paints, for example for wood or metal, as coating compositions, inter alia, for paper, wood, metal or plastic, as daylight-curable coatings for buildings and roadmarking, as powder coatings, for photographic reproduction processes, for holographic recording materials, for image recording processes or for the production of printing plates which can be developed using organic solvents or aqueous-alkaline media, for the production of masks for screen printing, as dental filling materials, as adhesives, as pressure-sensitive adhesives, as laminating resins, as etch resists or permanent resists and as solder masks for electronic circuits, for the production of three-dimensional articles by bulk curing (UV curing in transparent moulds) or by the stereolithography process, as described, for example, in U.S. Pat. No. 4,575,330, for the preparation of composite materials (for example styrenic polyesters, which may contain glass fibres and other assistants) and other thick-layer compositions, for the coating or encapsulation of electronic components or as coatings for optical fibres. The compounds according to the invention may also be used as initiators for emulsion polymerizations, as initiators of a polymerization for the fixing of ordered states of liquid-crystalline mono- and oligomers, and as initiators for the fixing of dyes to organic materials.

In surface coatings, mixtures of a prepolymer with polyunsaturated monomers are often used which also contain a monounsaturated monomer. The prepolymer here is primarily responsible for the properties of the coating film, and variation thereof allows the person skilled in the art to influence the properties of the cured film. The polyunsaturated monomer functions as a crosslinking agent which renders the coating film insoluble. The monounsaturated monomer functions as a reactive diluent by means of which the viscosity is reduced without the need to use a solvent.

Unsaturated polyester resins are mostly used in two-component systems in conjunction with a monounsaturated monomer, preferably styrene. For photoresists, specific one-component systems are frequently employed, for example polymaleimides, polychalcones or polyimides, as described in DE-A 2 308 830.

The compounds according to the invention and mixtures thereof may also be used as free-radical photoinitiators or photoinitiating systems for radiation-curable powder coatings. The powder coatings may be based on solid resins and monomers containing reactive double bonds, for example maleates, vinyl ethers, acrylates, acrylamides and mixtures thereof. A free-radically UV-curable powder coating can be formulated by mixing unsaturated polyester resins with solid acrylamides (e.g. methyl methacrylamidoglycolate) and with a free-radical photoinitiator according to the invention, as described, for example, in the paper "Radiation Curing of Powder Coatings", Conference Proceedings, Radtech Europe 1993 by M. Witrig and Th. Gohmann. Similarly, free-radically UV-curable powder coatings can be formulated by mixing unsaturated polyester resins with solid acrylates, methacrylates or vinyl ethers and with a photoinitiator (or mixture of photoinitiators) according to the invention. The powder coatings may also comprise binders as described, for example, in DE-A-42 28 514 or EP-A-636 669. The UV-curable powder coatings may also comprise white or coloured pigments. Thus, for example, preferably rutile titanium dioxide can be employed in concentrations of up to 50% by weight in order to give a cured powder coating having good covering power. The process normally comprises electrostatic or tribostatic spraying of the powder onto the substrate, for example of metal or wood, melting the powder by heating and, after a smooth film has been formed, radiation-curing of the coating using ultraviolet and/or visible light, for example with medium-pressure mercury lamps, metal halide lamps or xenon lamps. A particular advantage of the radiation-curable powder coatings over their heat-curable counterparts is that the flow time after the melting of the powder particles can be selectively extended in order to ensure the formation of a smooth, high-gloss coating. In contrast to heat-curable systems, radiation-curable powder coatings can be formulated without the unwanted effects of a reduction in their lifetime so that they melt at relatively low temperatures. For this reason, they are also suitable as coatings for heat-sensitive substrates such as wood or plastics.

In addition to the photoinitiators according to the invention, the powder coating formulations may also contain UV absorbers. Appropriate examples have been listed above unders items 1–8.

The photocurable compositions according to the invention are suitable, for example, as coating substances for substrates of all kinds, for example wood, textiles, paper, ceramic, glass, plastics such as polyesters, polyethylene terephthalate, polyolefins or cellulose acetate, especially in the form of films, and also metals such as Al, Cu, Ni, Fe, Zn, Mg or Co and GaAs, Si or $SiO_2$, on which it is desired to apply a protective coating or, by imagewise exposure, an image.

The substrates can be coated by applying a liquid composition, a solution or suspension to the substrate. The choice of the solvent and the concentration depend predominantly on the type of composition and the coating procedure. The solvent should be inert: in other words it should not undergo any chemical reaction with the components and should be capable of being removed again after the coating operation, in the drying process. Examples of suitable solvents are ketones, ethers and esters, such as methyl ethyl ketone, isobutyl methyl ketone, cyclopentanone, cyclohexanone, N-methylpyrrolidone, dioxane, tetrahydrofuran, 2-methoxyethanol, 2-ethoxyethanol, 1-methoxy-2-propanol, 1,2-dimethoxyethane, ethyl acetate, n-butyl acetate and ethyl 3-ethoxypropionate. Using known coating processes, the solution is applied evenly to a substrate, for example by spincoating, dip coating, knife coating, curtain coating, brushing, spraying—especially electrostatic spraying—and reverse roll coating. It is also possible to apply the photosensitive layer to a temporary, flexible support and then to coat the final substrate, for example a copper-laminated circuit board, by means of layer transfer via lamination.

The quantity applied (layer thickness) and the nature of the substrate (layer support) are functions of the desired application. The range of coat thicknesses generally comprises values from about 0.1 μm to more than 10 μm.

The radiation-sensitive compositions according to the invention find application as negative resists which have a very high photosensitivity and can be developed in an aqueous-alkaline medium without swelling. They are suitable as photoresists for electronics (galvanoresists, etch resists and solder resists), the production of printing plates such as offset printing plates or screen printing forms, and can be used for chemical milling or as microresists in the production of integrated circuits. There is a correspondingly wide range of variation in the possible layer supports and the processing conditions for the coated substrates.

Examples of the layer supports for photographic information recording are films made of polyester, cellulose acetate or plastic-coated paper; for offset printing plates, specially treated aluminium; for the production of printed circuits, copper-faced laminates, and for the production of integrated circuits, silicon wafers. The layer thicknesses for photographic materials and offset printing plates are generally from about 0.5 μm to 10 μm, while for printed circuits they are from 0.4 μm to about 2 μm.

Following the coating of the substrates, the solvent is generally removed by drying to leave a layer of the photoresist on the substrate.

The term "imagewise exposure" relates both to exposure through a photomask containing a predetermined pattern, for example a slide, exposure by a laser beam which is moved under control from a computer, for example, over the surface of the coated substrate, thereby generating an image, and to irradiation with computer-controlled electron beams.

Following the imagewise exposure of the material and prior to developing, it may be advantageous to carry out a brief thermal treatment, in which only the exposed parts are thermally cured. The temperatures employed are generally 50°–150° C. and preferably 80°–130° C.; the duration of the thermal treatment is generally between 0.25 and 10 minutes.

The photocurable composition can also be used in a process for the production of printing plates or photoresists as described, for example, in DE-A-4 013 358. In this process the composition is exposed before, simultaneously with or after the imagewise irradiation, exposure being carried out for a short period with visible light having a wavelength of at least 400 nm without a mask.

Following the exposure and the optional thermal treatment, the unexposed areas of the photoresist are removed using a developer in a manner known per se.

As already mentioned, the compositions according to the invention can be developed by aqueous-alkaline media. Suitable aqueous-alkaline developer solutions are, in particular, aqueous solutions of tetraalkylammonium hydroxides or of alkali metal silicates, phosphates, hydroxides and carbonates. Relatively small quantities of wetting agents and/or organic solvents may also be added, if desired, to these solutions. Examples of typical organic solvents which may be added in small quantities to the developing liquids are cyclohexanone, 2-ethoxyethanol, toluene, acetone and mixtures of such solvents.

Photocuring is of considerable importance for printing inks, since the drying time of the binder is a crucial factor for the production rate of graphic products and should be in the order of fractions of seconds. UV-curable inks are important, in particular, for screen printing.

As already mentioned, the mixtures according to the invention are also highly suitable for the production of printing plates, where, for example, mixtures of soluble, linear polyamides or styrene/butadiene or styrene/isoprene rubber, polyacrylates or polymethyl methacrylates containing carboxyl groups, polyvinyl alcohols or urethane acrylates are used with photopolymerizable monomers, for example acrylamides, methacrylamides, acrylates or methacrylates, and a photoinitiator. Films and plates made from these systems (wet or dry) are exposed through the negative (or positive) of the print original, and the uncured parts are subsequently washed out using a suitable solvent.

A further area of application for photocuring is in the coating of metals, for example in the coating of metal sheets and tubes, cans or bottle caps, and the photocuring of plastic coatings, for example PVC-based wall or floor coverings.

Examples of the photocuring of paper coatings are the colourless coating of labels, record sleeves or book covers.

The use of the compounds according to the invention for curing shaped articles made from composite compositions is likewise of interest. The composite composition is made up of a self-supporting matrix material, for example a glass-fibre fabric [cf. K.-P. Mieck and T. Reussmann in Kunststoffe 85 (1995), 366–370], which is impregnated with the photocuring formulation. Shaped articles which are produced from composite compositions, using the compounds according to the invention, are of high mechanical stability and resistance. The compounds according to the invention can also be employed as photocuring agents in moulding, impregnating and coating compositions, as described, for example, in EP-A-7086. Examples of such compositions are fine coating resins on which stringent requirements are placed with respect to their curing activity and yellowing resistance, or fibre-reinforced mouldings such as planar or longitudinally or transversely corrugated light diffusing panels. Processes for the production of such mouldings, for example hand lay-up, spray lay-up, centrifugal or filament winding processes, are described by, for example P. H. Selden in "Glasfaserverstärkte Kunststoffe" [Glass fibre-reinforced plastics], page 610, Springer Verlag Berlin-Heidelberg-New York 1967. Examples of articles which can be produced by this process are boats, chipboard or plywood panels coated on both sides with glass fibre-reinforced plastic, pipes, containers and the like. Other examples of moulding, impregnating and coating compositions are UP resin fine coatings for mouldings containing glass fibres (GRP), e.g. corrugated sheets and paper laminates. Paper laminates may also be based on urea or melamine resins. The fine coating is produced on a support (for example a film) prior to the production of the laminate. The photocurable compositions according to the invention can also be used for casting resins or for encapsulating articles such as electronic components and the like.

Curing employs medium-pressure mercury lamps as are conventional in UV curing. However, less intense lamps are also of particular interest, for example those of the type TL40W/03 or TL40W/05. The intensity of these lamps corresponds approximately to that of sunlight. Direct sunlight can also be used for curing. A further advantage is that the composite composition can be removed from the light source in a partially cured, plastic state and can be deformed. Curing is subsequently carried out to completion.

Also important is the use of photocurable compositions for imaging processes and for the optical production of information carriers. In these applications, the coat (wet or dry) applied to the support is irradiated—as already described above—with UV or visible light through a photomask and the unexposed areas of the coat are removed by treatment with a solvent (=developer). The photocurable layer can also be applied by electrodeposition to metal. The exposed areas are crosslinked/polymeric and thus insoluble and remain on the support. If appropriate colouration is carried out, visible images are formed. If the support is a metallized layer, then the metal can be removed from the unexposed areas by etching after exposure and development or can be increased in thickness by electroplating. In this way, printed electronic circuits and photoresists can be produced.

The photosensitivity of the compositions according to the invention generally ranges from the UV region (about 200 nm) up to about 600 nm, and therefore spans a very wide range. Suitable radiation comprises, for example, sunlight or light from artificial sources. Therefore, a large number of very different types of light source can be used. Both point sources and flat radiators (lamp carpets) are appropriate. Examples are carbon arc lamps, xenon arc lamps, medium-pressure, high-pressure and low-pressure mercury lamps, doped with metal halides if desired (metal halogen lamps), microwave-stimulated metal vapour lamps, excimer lamps, superactinic fluorescent tubes, fluorescent lamps, incandescent argon lamps, electronic flashlights, photographic flood lamps, electron beams and X-rays, produced by means of synchrotrons, or laser plasma. The distance between the lamp and the substrate according to the invention which is to be coated can vary depending on the application and on the type and/or power of the lamp, for example between 2 cm and 150 cm. Of particular suitability are laser light sources, for example excimer lasers, such as krypton F lasers for exposure at 248 nm. Lasers in the visible range may also be employed. In this case the high sensitivity of the materials according to the invention is very advantageous. By this method it is possible to produce printed circuits in the electronics industry, lithographic offset printing plates or relief printing plates, and photographic image recording materials.

The invention also specifically relates to the use of the above-described composition for the production of surface coating materials, printing inks, printing plates, dental compositions and resist materials and as image recording material, especially for holographic recordings.

The invention likewise specifically relates to a coated substrate which is coated on at least one surface with a composition as described above, and to a process for the photographic production of relief images, in which a coated substrate is subjected to imagewise exposure and then the unexposed areas are removed with a solvent.

The invention therefore also specifically relates to a method for the photopolymerization of compounds containing ethylenically unsaturated double bonds, which comprises irradiating a composition as described above with light in the range from 200 to 600 nm.

The examples which follow illustrate the invention in more detail. As in the remainder of the description and in the claims, parts or percentages are by weight unless stated otherwise. Where reference is made to alkyl radicals containing more than 3 carbon atoms without indicating specific isomers, they are always in the form of the n-isomers.

EXAMPLE 1

Preparation of tris(2-Methylbenzoyl)phosphine Oxide 5.0 g (0.02 mol) of tris(trimethylsilyl)phosphine are added dropwise at room temperature to a solution of 9.3 g of 2-methylbenzoyl chloride in 50 ml of dimethoxyethane. After 12 hours, the reaction solution is concentrated on a rotary evaporator. The residue is dissolved in 50 ml of toluene and, at 0° C., 2.3 g (0.02 mol) of 30% strength hydrogen peroxide solution are added. After stirring for 2 hours at 0° C., the reaction solution is washed once with water; and the organic phase is dried over magnesium sulfate, filtered and concentrated on a rotary evaporator. Recrystallization from ethanol gives the title compound with a melting point of 97°–98° C., Elemental analysis $C_{24}H_{21}O_4P$ (404.4)

calc.: C 71.28% H 5.23% found: C 69.90% H 5.20%

The shift value δ [ppm] in $^{31}$P-NMR, measured in $CDCl_3$, is 26.87 (s). The shift value δ [ppm] in $^1$H-NMR, measured in $CDCl_3$, are 2.57 (s), 7.26–7.54 (m) and 8.56 (d) J=7.7 Hz.

EXAMPLES 2–4

The compounds of the examples 2–4 are prepared according to the method described in example 1 employing the corresponding educts. The structures and physical data are listed in table 1.

TABLE 1

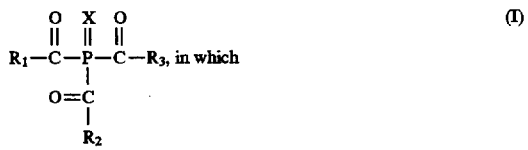

| Example | R₁ | R₂ | R₃ | melting point [°C.] | elemental analysis (calc. Found) C [%] | H [%] | ³¹P-NMR [ppm] |
|---------|------|------|------|-------------|-------|-------|---------|
| 2 | OCH₃ | H | H | 168–169 | 63.72 63.55 | 4.68 4.78 | 20.59* |
| 3 | CH₃ | CH₃ | H | 100–102 | 72.63 72.46 | 6.10 6.09 | 27.48** |
| 4 | CH₃ | H | CH₃ | 106–107 | 72.63 72.43 | 6.10 6.14 | 26.60** |

*determination in CDCl₃
**determination in Benzol (d₆)

EXAMPLE 5

Photopolymerization of Tripropylene Glycol Diacrylate

A 1% strength solution of the compound of Example 1 in tripropylene glycol diacrylate is prepared. The solution is irradiated with two lamps of type TL20W/03. After 30 s, spontaneous polymerization takes place to form a solid mass.

EXAMPLE 6

Polymerization of Hexanediol Diacrylate in Sunlight

A 1% strength solution of the compound of Example 1 in hexanediol diacrylate is prepared. The solution is exposed to sunlight. After 15 s, solidification takes place suddenly.

EXAMPLE 7

Photoinitiator Reactivity in a White Paint

The photoinitiator of Example 1 is incorporated in a concentration of 2% by weight into a white paint formulation comprising 67.5 parts of ®Ebecryl 830 (polyester acrylate from UCB, Belgium), 5.0 parts of hexanediol diacrylate, 2.5 parts of trimethylolpropane triacrylate and 25.0 parts, of titanium dioxide (R-TC2) of ruffle type.

The samples are applied to chipboard using a 100 μm slotted doctor knife and cured with an 80 W/cm medium-pressure mercury lamp (Hanovia type) at a belt speed of 3 m/min. The cured sample has a smearproof surface. The König hardness (DIN 53157) is 150 s.

EXAMPLE 8

Photocuring of a Glass Fibre Composite Composition

In a formulation comprising unsaturated polyester resin and styrene (®Vestopal X7231, Hüls, Germany), 2% of a mixture of 75% 2-hydroxy-2-methyl-1-phenylpropanone (compound of the formula V where R₁₅=H, R₁₆ and R₁₇=CH₃, R₁₈=OH) and 25% of the compound of Example 1 are dissolved. A laminate comprising 5 layers of glass fibre fabric (type: Interglasgewebe IG 9214 from Interglas, Germany) is impregnated with this solution. The weight ratio of glass to formulation is 3:2. The laminate is covered with a transparent plastic film and irradiated for 3 minutes under 5 lamps of type TL40W/03 at a distance of 15 cm. A very stable composite is obtained.

What is claimed is:

1. A compound of the formula I $$R_1-\overset{\overset{O}{\|}}{C}-\overset{\overset{X}{\|}}{\underset{\underset{R_2}{\underset{|}{C=O}}}{P}}-\overset{\overset{O}{\|}}{C}-R_3, \text{ in which} \qquad (I)$$

X is oxygen or sulfur,

R₁, R₂ and R₃ independently of one another are a group

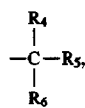

$C_2$–$C_8$alkenyl, phenyl which is unsubstituted or is substituted from one to four times with $C_1$–$C_{12}$alkyl, $C_1$–$C_{12}$alkoxy, $C_1$–$C_6$alkylthio and/or halogen, or are naphthyl which is unsubstituted or is substituted from one to four times with $C_1$–$C_{12}$alkyl, $C_1$–$C_{12}$alkoxy, $C_1$–$C_6$alkylthio and/or halogen, or are biphenyl which is unsubstituted or is substituted from one to four times with $C_1$–$C_{12}$alkyl, $C_1$–$C_{12}$alkoxy, $C_1$–$C_6$alkylthio and/or halogen, or R₁, R₂ and R₃ independently of one another are an O-, S- or N-containing 5- or 6-membered heterocyclic ring, $R_1$ is in addition a group of the formula II

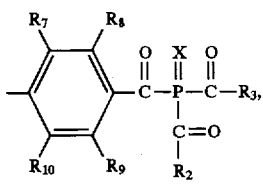

or $R_1$ and $R_2$ are linked to form a ring containing 4 to 10 carbon atoms which is unsubstituted or substituted by 1 to 6 $C_1$–$C_4$alkyl groups, $R_4$, $R_5$ and $R_6$ independently of one another are hydrogen or $C_1$–$C_{18}$alkyl, or $R_5$ and $R_6$, together with the carbon atom to which they are attached, form a cyclopropyl, cyclopentyl or cyclohexyl ring, and $R_7$, $R_8$, $R_9$ and $R_{10}$ independently of one another are hydrogen, $C_1$–$C_4$alkyl, $C_1$–$C_4$alkoxy or halogen.

2. A compound of the formula I according to claim 1, in which $R_1$, $R_2$ and $R_3$ independently of one another are a group

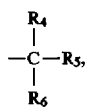

$C_2$–$C_6$alkenyl, naphthyl which is unsubstituted or is substituted from one to four times with $C_1$–$C_4$alkyl, $C_1$–$C_4$alkoxy or halogen, biphenyl which is unsubstituted or is substituted from one to four times with $C_1$–$C_4$alkyl, $C_1$–$C_4$alkoxy or halogen, or are a radical of the formula III

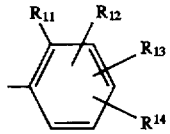

or are pyridyl, furyl, pyrrolyl or thienyl, $R_1$ in addition is a group of the formula II, or $R_1$ and $R_2$ are linked to form a benzene ring, $R_4$ and $R_5$ independently of one another are hydrogen or $C_1$–$C_{12}$alkyl, $R_6$ is $C_1$–$C_{12}$alkyl, or $R_5$ and $R_6$, together with the carbon atom to which they are attached, form a cyclopentyl or cyclohexyl ring, $R_7$, $R_8$, $R_9$ and $R_{10}$ independently of one another are methyl or methoxy, $R_{11}$ is $C_1$–$C_4$alkyl, $C_1$–$C_4$alkoxy, $C_1$–$C_4$alkylthio or halogen, and $R_{12}$, $R_{13}$ and $R_{14}$ independently of one another are hydrogen, $C_1$–$C_4$alkyl, $C_1$–$C_4$alkoxy, $C_1$–$C_4$alkylthio or halogen.

3. A compound of the formula I according to claim 2, in which $R_1$, $R_2$ and $R_3$ independently of one another are a group

$C_2$–$C_4$alkenyl, naphthyl which is unsubstituted or is substituted from one to four times with methyl, methoxy or chlorine, or are a radical of the formula III, $R_4$ is hydrogen, $R_5$ and $R_6$ are $C_1$–$C_7$alkyl, or $R_5$ and $R_6$, together with the carbon atom to which they are attached, form a cyclopentyl or cyclohexyl ring, $R_{11}$ is $C_1$–$C_4$alkyl, $C_1$–$C_4$alkoxy or chlorine, and $R_{12}$, $R_{13}$ and $R_{14}$ independently of one another are hydrogen, $C_1$–$C_4$alkyl, $C_1$–$C_4$alkoxy or chlorine.

4. A compound of the formula I according to claim 3, in which $R_1$, $R_2$ and $R_3$ are identical and are tert-butyl, $C_2$–$C_4$alkenyl or a radical of the formula III, $R_{11}$ is methyl, methoxy or chlorine, and $R_{12}$, $R_{13}$ and $R_{14}$ independently of one another are hydrogen, methyl, methoxy or chlorine.

5. A compound of the formula I according to claim 1, in which $R_1$, $R_2$ and $R_3$ are identical and are a radical of the formula IV

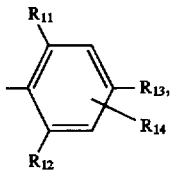

$R_{11}$ is methyl, methoxy or chlorine, $R_{12}$ is hydrogen, $R_{13}$ is hydrogen or methyl, and $R_{14}$ is hydrogen.

6. A compound according to claim 1 in which X is oxygen.

7. A composition comprising (a) at least one ethylenically unsaturated photopolymerizable compound, and (b) as photoinitiator, at least one compound of the formula I as defined in claim 1.

8. A composition according to claim 7, which contains other photoinitiators and/or additives in addition to component (b).

9. A composition according to claim 7, containing 0.05–15% by weight of component (b), based on the composition.

10. A composition according to claim 9 containing 0.1–5% by weight of component (b) based on the composition.

11. A composition according to claim 8, in which the additional photoinitiators are compounds of the formula V

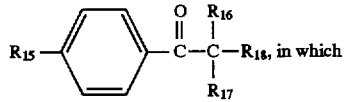

$R_{15}$ is hydrogen, $C_1$–$C_{18}$alkyl, $C_1$–$C_{18}$alkoxy, —$OCH_2CH_2$—$OR_{19}$, a group

or a group

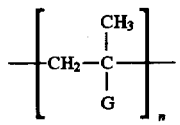

in which n has a value from 2 to 10 and and G is the radical

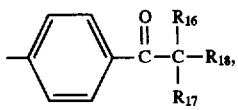

$R_{16}$ and $R_{17}$ independently of one another are hydrogen, $C_1$–$C_6$alkyl, phenyl, $C_1$–$C_{16}$alkoxy or —O(CH$_2$CH$_2$O)$_m$—$C_1$–$C_{16}$alkyl in which m is a number from 1–20, or $R_{16}$ and $R_{17}$, together with the carbon atom to which they are attached, form a cyclohexyl ring, $R_{18}$ is hydroxyl, $C_1$–$C_{16}$alkoxy or —O(CH$_2$CH$_2$O)$_m$—$C_1$–$C_{16}$alkyl, $R_{16}$, $R_{17}$ and $R_{18}$ not all simultaneously being $C_1$–$C_{16}$alkoxy or —O(CH$_2$CH$_2$O)$_m$—$C_1$–$C_{16}$alkyl, and $R_{19}$ is hydrogen,

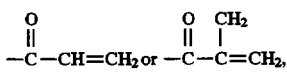

or in which the additional photoinitiators are compounds of the formula VI

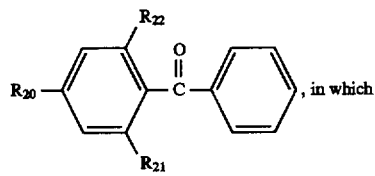

$R_{20}$, $R_{21}$ and $R_{22}$ independently of one another are hydrogen or methyl, or in which the additional photoinitiators are mixtures of compounds of the formulae V and/or VI.

12. A composition according to claim 11, in which $R_{16}$ and $R_{17}$ in the formula V are independently of one another $C_1$–$C_6$alkyl or, together with the carbon atom to which they are attached, form a cyclohexyl ring, and $R_{18}$ is hydroxyl.

13. A composition according to claim 11, in which the proportion of compounds of the formula I in the mixture with compounds of the formulae V and/or VI is from 5 to 95%.

14. A composition according to claim 13, in which the proportion of compounds of the formula I in the mixture with compounds of formulae V and/or VI is from 30 to 70% by weight.

15. A composition according to claim 11, in which $R_{16}$ and $R_{17}$ in the compounds of the formula V are identical and are methyl, and $R_{18}$ is hydroxyl or isopropoxy.

16. A composition according to claim 13, comprising compounds of the formula I and a mixture of compounds of the formula VI in which compounds of the formula VI where $R_{20}$ and $R_{21}$ are hydrogen and $R_{22}$ is methyl are present to the extent of 20% and compounds of the formula VI where $R_{20}$, $R_{21}$ and $R_{22}$ are methyl are present to the extent of 80%.

17. A photoinitiator for the photopolymerization of ethylenically unsaturated compounds comprising a compound of formula I according to claim 1.

18. A method for the photopolymerization of compounds containing ethylenically unsaturated double bonds, which comprises irradiating a composition according to claim 7 with light in the range from 200 to 600 nm.

19. A method according to claim 18, which is carried out by the method of bulk curing or stereolithography.

20. A method according to claim 18 wherein the irradiated composition is in the form of a coating upon a substrate.

21. A method of claim 20 wherein said coating is selected from powder coatings, composite coatings, printing plate coatings, masks for screen printing, photoresists for printed electronic circuits, adhesives, coatings for optical fibres, coatings or encapsulations of electronic components, white paints for wood and metal, clear coatings for day-light curable construction materials and road markings.

* * * * *